United States Patent
Hofen et al.

(10) Patent No.: US 6,646,141 B2
(45) Date of Patent: Nov. 11, 2003

(54) PROCESS FOR THE EPOXIDATION OF OLEFINS

(75) Inventors: Willi Hofen, Rodenbach (DE); Georg Thiele, Hanau (DE); Alexander Möller, Gelnhausen (DE)

(73) Assignees: Degussa AG, Düsseldorf (DE); UHDE GmbH, Dortmund (DE)

( * ) Notice: Subject to any disclaimer, the term of this patent is extended or adjusted under 35 U.S.C. 154(b) by 0 days.

(21) Appl. No.: 10/203,184

(22) PCT Filed: Feb. 3, 2001

(86) PCT No.: PCT/EP01/01166
§ 371 (c)(1),
(2), (4) Date: Oct. 4, 2002

(87) PCT Pub. No.: WO01/57010
PCT Pub. Date: Aug. 9, 2001

(65) Prior Publication Data
US 2003/0114694 A1 Jun. 19, 2003

(30) Foreign Application Priority Data
Feb. 7, 2000 (EP) ............................................. 00102544

(51) Int. Cl.[7] ...................... C07D 301/12; C07D 301/32
(52) U.S. Cl. ...................................... 549/531; 549/541
(58) Field of Search ................................ 549/531, 541

(56) References Cited

U.S. PATENT DOCUMENTS

| | | |
|---|---|---|
| 2,870,171 A | 1/1959 | Gable |
| 4,410,501 A | 10/1983 | Taramasso et al. |
| 4,833,260 A | 5/1989 | Neri et al. |
| 5,523,426 A | 6/1996 | Jubin, Jr. et al. |
| 5,591,875 A | 1/1997 | Chang et al. |
| 5,599,955 A | 2/1997 | Vora et al. .................. 549/525 |
| 5,620,935 A | 4/1997 | Thiele |
| 5,675,026 A | 10/1997 | Thiele |
| 5,760,253 A | 6/1998 | Danner et al. |
| 5,849,937 A | 12/1998 | Jubin, Jr. et al. |
| 5,849,938 A | 12/1998 | Rueter et al. |
| 5,912,367 A | 6/1999 | Chang |
| 6,042,807 A | 3/2000 | Faraj |
| 6,063,941 A | 5/2000 | Gilbeau |
| 6,372,924 B2 | 4/2002 | Thiele |

FOREIGN PATENT DOCUMENTS

| | | |
|---|---|---|
| DE | 196 23 611 | 12/1997 |
| DE | 197 23 950 | 12/1998 |
| DE | 197 54 185 | 2/1999 |
| DE | 198 35 907 | 2/2000 |
| EP | 0 100 118 | 2/1984 |
| EP | 0 100 119 | 2/1984 |
| EP | 0 106 671 | 4/1984 |
| EP | 0 230 349 | 7/1987 |
| EP | 0 230 949 | 8/1987 |
| EP | 0 568 336 | 11/1993 |
| EP | 0 568 337 | 11/1993 |
| EP | 0 583 828 | 2/1994 |
| EP | 0 645 473 | 3/1995 |

(List continued on next page.)

*Primary Examiner*—Ba K. Trinh
(74) *Attorney, Agent, or Firm*—Smith, Gambrell & Russell

(57) ABSTRACT

The present invention relates to a process for the working up of a product stream from the epoxidation of olefins that contains olefin, olefin oxide, water-miscible organic solvent and water, by separating this product stream into an overhead product containing olefin, olefin oxide and organic solvent, and into a bottom product containing organic solvent and water, wherein the separation takes place in a pre-evaporator with at most 5 theoretical separation stages, and 20 to 60% of the total amount of organic solvent introduced with the product stream is removed with the overhead product and the residue remains in the bottom product, as well as a process for the epoxidation of olefins that includes this working up stage.

12 Claims, 1 Drawing Sheet

FOREIGN PATENT DOCUMENTS

| | | |
|---|---|---|
| EP | 0 659 473 | 6/1995 |
| EP | 0 712 852 | 5/1996 |
| EP | 0 719 768 | 7/1996 |
| EP | 0 757 045 | 2/1997 |
| EP | 0 795 537 | 9/1997 |
| EP | 0 827 765 | 3/1998 |
| EP | 0 930 308 | 7/1999 |
| EP | 0 936 219 | 8/1999 |
| EP | 1 066 711 | 12/1999 |
| EP | WO 00/07695 | 2/2000 |
| EP | 1 122 248 | 8/2001 |
| EP | 1 138 387 | 10/2001 |
| EP | 1 221 442 | 7/2002 |
| JP | 2166636 | 6/1990 |
| WO | WO 97/47613 | 12/1997 |
| WO | WO 97/47614 | 12/1997 |
| WO | WO 99/01445 | 1/1999 |
| WO | WO 99/07690 | 2/1999 |
| WO | WO 99/11639 | 3/1999 |
| WO | WO 99/66696 | 12/1999 |
| WO | WO 00/17178 | 3/2000 |

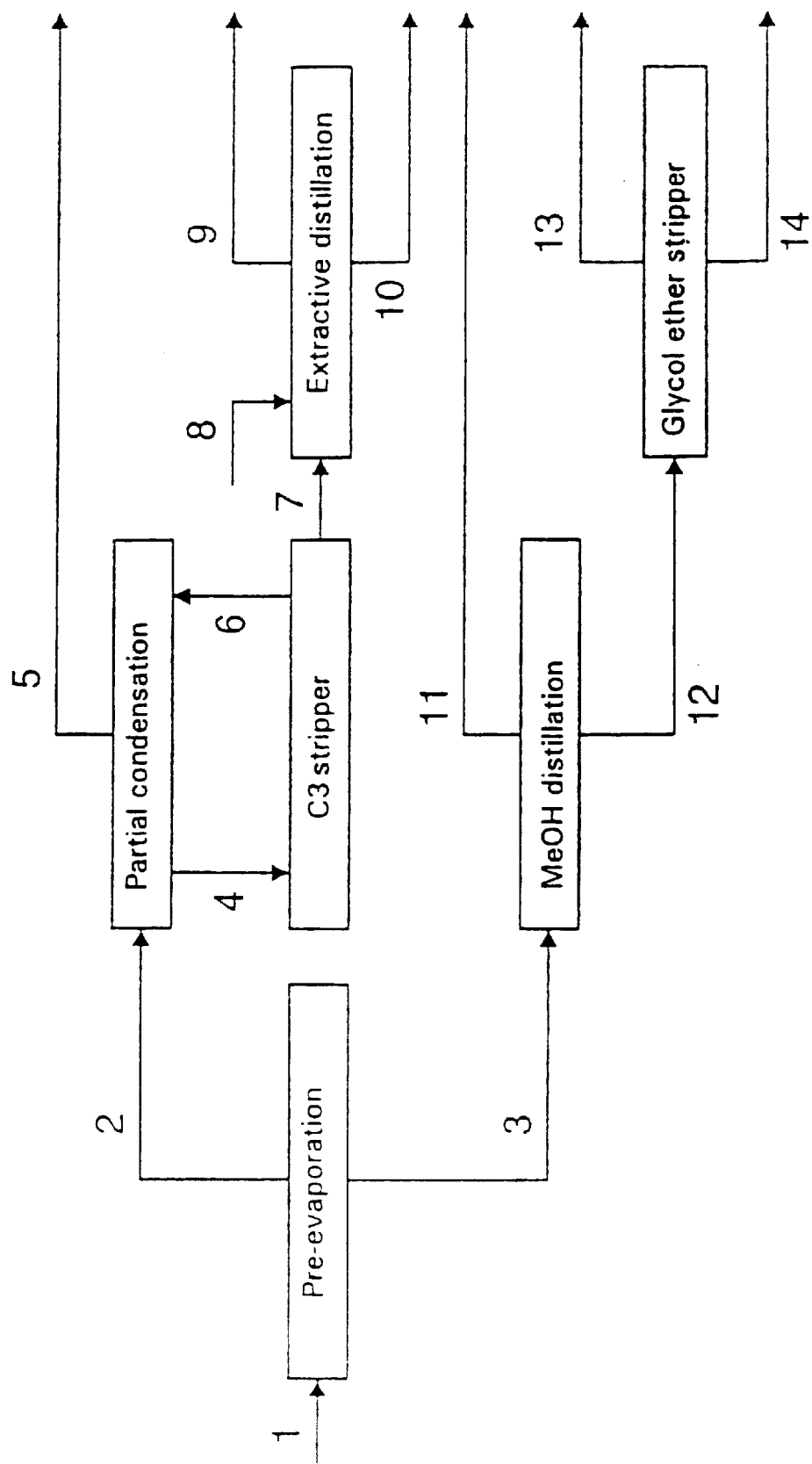

PROCESS FOR THE EPOXIDATION OF OLEFINS

This application is a 371 of PCT/EP01/01166, filed Feb. 3, 2000.

The present invention relates to a process for the epoxidation of olefins, in particular to the working up of the product stream from the epoxidation reaction.

PRIOR ART

From EP-A 100 118 it is known that propene can be converted with hydrogen peroxide into propene oxide if titanium silicalite is used as catalyst. The reaction is preferably carried out in the presence of a water-miscible solvent in order to improve the solubility of propene in the reaction mixture. Preferably solvents are used that have a boiling point between the boiling points of propene oxide and water in order to be able to separate the solvent from the reaction mixture by a distillation stage and recycle it to the reaction. Methanol is preferably used as solvent.

From U.S. Pat. No. 5,599,955 it is known that the reaction mixture which is obtained in the epoxidation reaction and which consists of propene oxide, propene, possibly propane, solvent and water can be separated by a succession of distillation steps, in which the mixture is separated in a first distillation step into an overhead product containing propene oxide, propene, and possibly propane, and into a bottom product containing the solvent and water. The efficient separation of propene oxide and solvent in a distillation step requires a large number of separation stages and a high reflux ratio in the distillation column.

WO-A 99/07690 describes a process for the purification of a methanol-containing product stream from the epoxidation of propene that also contains acetaldehyde as an impurity. In this case the crude product stream from the epoxidation is subjected to a fractional distillation, in which connection it is particularly important that methanol is present in sufficient amount in the overhead product in order to achieve a substantially complete transfer of acetaldehyde to the bottom product. To this end the concentration of methanol in the overhead product is 2–6 wt. %. A distillation column with 20–60 separation stages and a reflux ratio of between 10:1 and 30:1 is furthermore necessary in order to achieve the best possible quantitative separation of the acetaldehyde. This arrangement accordingly involves high investment and operating costs for the distillation column.

From U.S. Pat. No. 5,849,938 it is known that in the distillative working up of the methanol-containing reaction mixture from the propene epoxidation, the difference in volatilities of propene oxide and methanol can be increased by carrying out the distillation as an extractive distillation using water or propylene glycol as extraction agent. The purpose of this extractive distillation is to separate methanol as well as further high boiling point impurities as quantitatively as possible from the desired product, namely propene oxide, in one distillation step. This requires a large number of separation stages and a high reflux ratio in the distillation column. In order to achieve the desired separation result, at least 10 theoretical trays, preferably 20–60 theoretical trays are required with a reflux ratio in the range from 5:1 to 15:1. The working examples disclose 25 or 50 theoretical trays and a reflux ratio of 1:9 for the extraction distillation column.

In the known processes for the epoxidation of propene with $H_2O_2$ and titanium silicalite followed by distillative working up of the reaction mixture, due to the large number of separation steps and the high reflux ratio the residence time of propene oxide in the sections of the distillation column is long and there are also high concentrations of water and higher boiling point byproducts in the said sections, and accordingly the temperature is considerably higher than the boiling point of propene oxide under the distillation conditions. It has now been found that, as a result, there is an increased level of secondary reactions of propene oxide with water and other substances containing hydroxyl groups in the reaction mixture, which leads to undesirable losses of propene oxide. This disadvantage is particularly serious if the distillation is carried out under elevated pressure and thus at elevated temperature, which is advantageous for industrial exploitation since propene oxide can then be condensed with cooling water at the head of the distillation column and no expensive and energy-intensive cooling units have to be used.

This disadvantage of the known processes is exacerbated still further if the titanium silicalite catalyst used for the epoxidation reaction passes together with the reaction mixture into the separation column, since the catalyst also accelerates the undesirable secondary reactions of propene oxide with water and/or with other substances containing hydroxyl groups. If the epoxidation reaction is carried out with a suspended titanium silicalite catalyst, then in the known processes this catalyst must therefore be removed completely from the reaction mixture before the distillative separation of propene oxide and solvent. The separation of the catalyst at this point is particularly complicated since the separation is carried out in the presence of the highly volatile and carcinogenic substance propene oxide, and expensive and complicated industrial safety measures are therefore necessary. Also, precautions have to adopted in the known processes when using a fixed bed catalyst, for example by employing filtration, in order to prevent catalyst abrasion products settling in the distillation column and thereby causing product losses on account of the catalysis of the secondary reactions of propene oxide with water and/or other substances containing hydroxyl groups.

The object of the present invention is accordingly to provide a process for the working up of the product stream from the epoxidation of olefins in which the losses of epoxidation product can be reduced.

SUBJECT OF THE INVENTION

This object is achieved by a process for the working up of a product stream from the epoxidation of olefins that contains olefin, olefin oxide, water-miscible organic solvent and water, by separating this product stream into an overhead product containing olefin, olefin oxide and organic solvent, and into a bottom product containing organic solvent and water, wherein the separation takes place in a pre-evaporator with a maximum of 5 theoretical separation stages and 20 to 60% of the total amount of organic solvent entrained in the product stream is removed with the overhead product, the residue remaining in the bottom product.

This object is furthermore achieved by a process for the catalytic epoxidation of olefins in which the olefin is reacted in a reaction step with aqueous hydrogen peroxide in a water-miscible organic solvent in the presence of a titanium silicalite catalyst, the product stream from the reaction step being optionally added to a pressure release step and then worked up according to the aforedescribed process without prior distillative separation.

It has now been found that in the epoxidation of olefins with hydrogen peroxide and a titanium silicalite catalyst using an organic water-miscible solvent, the losses of olefin oxide in the distillative working up of the reaction mixture can be reduced if the processes according to the invention are employed.

DESCRIPTION OF THE INVENTION

The processes according to the invention are particularly suitable for the epoxidation of olefins having two to six carbon atoms, propene being particularly preferred. The epoxidation reaction of olefins according to the invention is described hereinafter with the example of propene as preferred olefin.

The epoxidation reaction with hydrogen peroxide is carried out in the presence of a titanium silicalite catalyst in an organic water-miscible solvent. For the epoxidation of propene a solvent is preferably chosen whose boiling point is between the boiling points of propene oxide and water. Suitable solvents include, inter alia, alcohols, for example methanol, ethanol or tert.-butanol, ethers, for example tetrahydrofuran or 1,2-dimethoxyethane, and ketones, for example acetone. Methanol is preferably used as solvent.

Due to recycling of substances in the process, the solvent used may contain 0 to 20 wt. % of water. Hydrogen peroxide is used as an aqueous solution containing 10 to 70 wt. % of hydrogen peroxide. A hydrogen peroxide crude product obtained from the extraction step of the anthraquinone process and containing 30 to 45 wt. % of hydrogen peroxide is preferably used. Propene may be used mixed with propane in an amount of between 0 and 10 vol. % of propane.

In one embodiment of the invention the titanium silicalite catalyst is suspended in the reaction mixture during the reaction. The catalyst is then used in the form of a powder or in the form of a suspendable granular material that has been produced by forming in a manner known per se, for example by spray drying or fluidised bed granulation. When using a suspended catalyst, flow mixing reactors, for example stirred tank reactors or recycle reactors, as well as non-flow mixing reactors, for example tubular flow reactors, may be used for the reaction. A cascade consisting of one to three flow mixing reactors and a non-flow mixing reactor connected downstream is preferably used.

In another embodiment of the invention the titanium silicalite catalyst is used as a fixed bed over which a mixture of the feedstock materials is passed. The catalyst is then used in the form of formed bodies that have been produced in a manner known per se, for example by extrusion with the addition of binders. When using a fixed bed catalyst, reactors with bubble column characteristics are preferably used, i.e. a continuous liquid phase and a dispersed gaseous phase simultaneously flow through the reactor.

The epoxidation reaction is carried out at temperatures between 0 and 80° C., preferably between 40 and 65° C., and at elevated pressures of 10 to 20 bar under an atmosphere substantially consisting of propene. The propene is used in excess and the residence time in the reactor is chosen so that a hydrogen peroxide conversion of more than 90%, preferably more than 95%, is achieved. The amount of solvent used is preferably chosen so as to achieve a ratio of 1 to 5 parts by weight of solvent to one part by weight of aqueous hydrogen peroxide solution.

Before the working up stage the pressure of the reaction mixture is preferably released in a pressure release stage to the pressure employed in the working up of the propene oxide. Part of the propene dissolved in the reaction mixture and possibly propane is gassed out. The resultant gas is recompressed via a compressor to the pressure prevailing in the reactor and is returned to the reaction, the propene oxide still contained in the gas preferably being removed via an absorption column together with the solvent used for the reaction, before the compression.

The reaction mixture is then separated in a pre-evaporator into an overhead product containing propene, possibly propane, propene oxide and solvent, and into a bottom product containing solvent, water, higher boiling point byproducts, such as for example propylene glycol, and possibly suspended titanium silicalite catalyst. The pre-evaporator according to the invention has at most only 5 theoretical separation steps and is preferably designed so that the stripping section corresponds to a simple evaporation and the remaining separation effect is achieved in the rectification section. The pre-evaporator is operated at a reflux ratio of at most 1.5 and if desired may also be operated totally without reflux. The pressure in the pre-evaporator is preferably chosen in the range from 3 to 8 bar in order to be able to condense the propene oxide together with cooling water from the overhead product without having to use a cooling unit. The pre-evaporator is operated according to the invention so that between 20 and 60% of the amount of solvent fed in with the reaction mixture is removed with the overhead product and the residue remains in the bottom product. In the operational procedure according to the invention more than 95%, typically more than 98% and preferably more than 99% of the propene oxide fed in is contained in the overhead product, and more than 90%, typically more than 97% and preferably more than 99% of the water fed in is contained in the bottom product.

The product stream from the reaction step normally contains 0.5–10 wt. % of propene, 0–4 wt. % of propane, 5–35 wt. % of propene oxide, 35–80 wt. % of methanol, 10–40 wt. % of water, 0.1–8 wt. % of higher boiling point byproducts, and 0–5 wt. % of titanium silicalite catalyst. This product stream is separated in the process according to the invention into an overhead product containing 1–25 wt. % of propene, 0–10 wt. % of propane, 15–75 wt. % of propene oxide, 25–85 wt. % of methanol and 0–3 wt. % of water, and into a bottom product containing 0–2 wt. % of propene oxide, 30–80 wt. % of methanol, 15–65 wt. % of water, 0.1–10 wt. % of higher boiling point byproducts, and 0–10 wt. % of titanium silicalite catalyst.

The overhead product is preferably only partially condensed and the uncondensed propene, possibly mixed with propane, is recompressed via a compressor to the pressure prevailing in the reaction part and is recycled to the reaction, the propene oxide still contained in the gas preferably being removed via an absorption column together with the solvent used for the reaction, before the compression. The propene still dissolved in the condensate and possibly propane are stripped out from the condensate in a C3 stripper and the stripped-out gas is recycled to the partial condenser. The mixture of propene oxide and solvent contained in the C3 stripper is separated by distillation into a propene oxide crude product, which can be purified further in a manner known per se, and the solvent, which is recycled to the epoxidation reaction.

In a particularly preferred embodiment the mixture of propene oxide and solvent, preferably methanol, obtained from the C3 stripper is worked up further by extractive distillation to achieve as quantitative a separation as possible of the solvent. In this connection the mixture of propene oxide and methanol is added to the middle section of an extractive distillation column, preferably at a point corresponding to ⅓ of the total number of theoretical trays counting from the bottom, and a polar solvent with hydroxyl functionality and having a boiling point higher than that of methanol is added to the extractive distillation column at a point above the point at which the condensate enters, preferably at a point corresponding to ⅔ of the total number of theoretical trays counting from the bottom. The propene oxide crude product is distilled off at the head of the column and a mixture of methanol and the polar solvent is extracted as bottom product. The polar solvent is selected from water, glycols, glycol ethers and mixtures thereof. The preferred polar solvent is water since in this case the mixture of water and methanol can be recycled directly to the reaction step without further purification.

In order to achieve as complete a separation of the methanol as possible, a column with 25–100 theoretical separation steps and with a reflux ratio of 1–4 is already sufficient on account of the concentration of the propene oxide in the overhead product, the mathematical product of the number of separation steps and the reflux ratio typically being 75 to 125.

On account of the pre-evaporation according to the invention, according to the preferred embodiment of the process according to the invention only a very small reflux ratio for the extractive distillation step is still necessary in order to achieve the desired separation effect. Despite the two-stage procedure the operating costs for separating the water and solvent are thereby reduced compared to the prior art.

A particularly preferred embodiment of the present invention accordingly relates to a process for the catalytic epoxidation of propene in which a) in a reaction step the propene is reacted with aqueous hydrogen peroxide in methanol in the presence of a titanium silicalite catalyst, b) the product stream from the reaction step is optionally passed to a pressure release step, and c) the product stream is then separated, without prior distillative separation, in a pre-evaporator having at most 5 theoretical separation steps into an overhead product containing propene, propene oxide and methanol, and into a bottom product containing methanol and water, 20 to 60% of the total amount of methanol introduced into the product stream being removed with the overhead product and the residue remaining in the bottom product, d) the overhead product from step c) is at least partially condensed, the condensate containing, optionally after stripping out propene and any propane present

| | |
|---|---|
| 0–12 | wt. % propene, |
| 0–5 | wt. % propane, |
| 15–75 | wt. % propene oxide, |
| 25–85 | wt. % methanol and |
| 0–3 | wt. % water, and | e) the condensate from step d) is subjected to an extractive distillation, wherein e1) the condensate is added to a middle section of an extractive distillation column, e2) a polar solvent with hydroxyl functionality and having a boiling point higher than that of methanol is added to the extractive distillation column at a point above the point at which the condensate enters, e3) propene oxide is distilled off at the head of the column, and e4) a bottom product containing methanol and the polar solvent is removed.

The bottom product from the pre-evaporator is separated in a further distillation step into the solvent, which is returned to the epoxidation reaction, and into a mixture of water and high boiling point byproducts, which is either worked up further or is discharged.

When using a suspended titanium silicalite catalyst the catalyst is recovered from the bottom product of the pre-evaporator by solid/liquid separation, for example by filtration or centrifugation, in which connection the solid/liquid separation can be carried out as desired either before or after the recovery of the solvent. A separation of the catalyst at this point of the process is particularly advantageous since the propene oxide, which represents a health hazard, has at this point already been separated and less stringent requirements are therefore placed on industrial safety, which considerably simplifies the overall process and makes it much more cost-effective.

FIG. 1 illustrates the working up of the reaction mixture for a particularly preferred embodiment of the invention using a fixed bed catalyst and methanol as solvent. The reaction mixture 1 obtained from the reaction after release of pressure is separated in the pre-evaporation stage according to the invention into an overhead product 2 containing propene, propane, propene oxide and methanol, and a bottom product 3 containing methanol, propylene glycol monomethyl ether, water and high boiling point compounds. A liquid condensate 4 that contains propene oxide and methanol as well as propene and propane dissolved therein is obtained from the vapour state overhead product 2. The uncondensed stream 5, which substantially consists of propene and propane, is returned to the epoxidation reaction. The propene and propane dissolved in the condensate 4 are stripped from the latter in the C3 stripper and returned in the vapour state together with the stream 6 to the partial condensation stage. The stream 7, which consists substantially of propene oxide and methanol and has been freed from propene and propane, is separated in an extractive distillation in which water is fed in as extraction agent immediately underneath the head of the column together with the stream 8, into a propene oxide crude product 9 that consists of more than 98%, typically more than 99.5%, of propene oxide, and into a bottom product 10 that consists substantially of methanol and water, the water content being typically less than 20% The bottom product 10 is returned as solvent to the epoxidation reaction. The bottom product 3 obtained in the pre-evaporator is separated in a distillation stage for recovering methanol, into an overhead product 11 that typically consists of more than 95% of methanol, and into a bottom product 12 consisting of propylene glycol monomethyl ethers, water and high boiling point compounds. The overhead product 11 is returned as solvent to the epoxidation reaction, in which connection it may optionally be combined together with the stream 10. From the stream 12 the propylene glycol monomethyl ethers are separated as an azeotrope with water in a stripping column, together with the stream 13. The remaining stream 14, consisting of water and high boiling point compounds, is passed for waste treatment.

The process according to the invention has the advantage compared to the prior art that in the working up the duration of the thermal stresses to which the olefin oxide is subjected in the presence of water and other potential reactants is substantially shorter and therefore the loss of olefin oxide by secondary reactions in the working up is significantly reduced.

In the preferred embodiment according to FIG. 1 the process according to the invention also has the advantage that the separation of the propene oxide from methanol and water can be achieved with smaller reflux ratios in the columns than in the prior art, which leads to savings in operating costs. With the extractive distillation that is used to separate propene oxide and methanol there is also the advantage, compared to the prior art, that the methanol-water mixture obtained in the bottom of the column can be returned as solvent directly to the epoxidation process, with the result that no separate distillation column is required to recover the extraction agent.

When using a suspended titanium silicalite catalyst it is possible with the process according to the invention, in contrast to the prior art, to separate the propene oxide from the reaction mixture before the recovery of the catalyst by solid/liquid separation takes place. Considerable savings in the necessary industrial safety measures are possible thanks to the solid/liquid separation in the absence of the carcinogenic propene oxide.

What is claimed is:

1. Process for the working up of a product stream from the epoxidation of olefins that contains olefin, olefin oxide, water-miscible organic solvent and water, by separating this product stream into an overhead product containing olefin, olefin oxide and organic solvent, and into a bottom product containing organic solvent and water, characterised in that the separation is carried out in a pre-evaporator with at most 5 theoretical separation stages and 20 to 60% of the total amount of organic solvent introduced with the product stream is removed with the overhead product and the residue remains in the bottom product.

2. Process according to claim 1, characterised in that the reflux ratio in the pre-evaporator is at most 1.5.

3. Process according to claim 1, characterised in that more than 95%, preferably more than 98% and particularly preferably more than 99% of the entrained olefin oxide is removed with the overhead product, and more than 90%, preferably more than 97% and particularly preferably more than 99% of the entrained water is removed with the bottom product.

4. Process for the catalytic epoxidation of olefins in which in a reaction step the olefin is reacted with aqueous hydrogen peroxide in an organic water-miscible solvent in the presence of a titanium silicalite catalyst, wherein the product stream from the reaction step is optionally fed to a pressure release step and is then worked up, without prior distillative separation, according to the process of claim 1.

5. Process according to claim 4, characterised in that the olefin is selected from a $C_2$–$C_6$ olefin and is preferably propene, and the solvent is selected from alcohols, ethers and ketones, and is preferably methanol.

6. Process according to claim 5, characterised in that the product stream from the reaction stage contains:

| | |
|---|---|
| 0.5–10 | wt. % propene |
| 0–4 | wt. % propane |
| 5–35 | wt. % propene oxide |
| 35–80 | wt. % methanol |
| 10–40 | wt. % water |
| 0.1–8 | wt. % byproducts |
| 0–5 | wt. % titanium silicalite catalyst, | the overhead product from the pre-evaporator contains

| | |
|---|---|
| 1–25 | wt. % propene |
| 0–10 | wt. % propane |
| 15–75 | wt. % propene oxide |
| 25–85 | wt. % methanol |
| 0–3 | wt. % water | and the bottom product from the pre-evaporator contains

| | |
|---|---|
| 0–2 | wt. % propene oxide |
| 30–80 | wt. % methanol |
| 15–65 | wt. % water |
| 0.1–10 | wt. % byproducts |
| 0–10 | wt. % titanium silicalite catalyst. |

7. Process according to claim 4, characterised in that the overhead product from the pre-evaporator is at least partially condensed, constituents having a boiling point that is lower than that of olefin oxide are optionally stripped from the condensate, and the condensate is then subjected to an extractive distillation.

8. Process according to claim 4, characterised in that the titanium silicalite catalyst is present suspended in the reaction mixture.

9. Process according to claim 8, characterised in that the bottom product from the pre-evaporator contains titanium silicalite catalyst that is separated by solid/liquid separation.

10. Process according to claim 4, characterised in that the titanium silicalite catalyst is present as a fixed bed.

11. Process for the catalytic epoxidation of propene, in which
 a) in a reaction step the propene is reacted with aqueous hydrogen peroxide in methanol in the presence of a titanium silicalite catalyst,
 b) the product stream from the reaction step is optionally passed to a pressure release step, and
 c) the product stream is then separated, without prior distillative separation, in a pre-evaporator having at most 5 theoretical separation steps into an overhead product containing propene, propene oxide and methanol, and into a bottom product containing methanol and water, 20 to 60% of the total amount of methanol introduced with the product stream being removed with the overhead product and the residue remaining in the bottom product,
 d) the overhead product from step c) is at least partially condensed, the condensate containing, optionally after stripping out propene and any propane present

| | |
|---|---|
| 0–12 | wt. % propene, |
| 0–5 | wt. % propane, |
| 15–75 | wt. % propene oxide, |
| 25–85 | wt. % methanol and |
| 0–3 | wt. % water, and | e) the condensate from step d) is subjected to an extractive distillation, wherein
  e1) the condensate is added to a middle section of an extractive distillation column,
  e2) a polar solvent with hydroxyl functionality and having a boiling point that is higher than that of methanol is added to the extractive distillation column at a point above the point at which the condensate enters,
  e3) propene oxide is distilled off at the head of the column, and
  e4) a bottom product containing methanol and the polar solvent is removed.

12. Process according to claim 11, characterised in that the polar solvent is selected from water, glycols, glycol ethers and mixtures thereof.

* * * * *

UNITED STATES PATENT AND TRADEMARK OFFICE
CERTIFICATE OF CORRECTION

PATENT NO. : 6,646,141 B1
DATED : November 11, 2003
INVENTOR(S) : Hofen, Willi et al.

It is certified that error appears in the above-identified patent and that said Letters Patent is hereby corrected as shown below:

Title page,
Item [56], References Cited, FOREIGN PATENT DOCUMENTS, should read as follows:

| | | | | | |
|---|---|---|---|---|---|
| FOREIGN PATENT DOCUMENTS | | | EP | 1 122 248 | 8/2001 |
| | | | EP | 1 138 387 | 10/2001 |
| EP | 0 659 473 | 6/1995 | EP | 1 221 442 | 7/2002 |
| EP | 1 712 852 | 5/1996 | JP | 216663 | 6/1990 |
| EP | 0 719 768 | 7/1996 | WO | WO 97/47613 | 12/1997 |
| EP | 0 757 045 | 2/1997 | WO | WO 97/47614 | 12/1997 |
| EP | 0 795 537 | 9/1997 | WO | WO 99/01445 | 1/1999 |
| EP | 0 827 765 | 3/1998 | WO | WO 99/07690 | 2/1999 |
| EP | 0 930 308 | 7/1999 | WO | WO 99/11639 | 3/1999 |
| EP | 0 936 219 | 8/1999 | WO | WO 99/66696 | 12/1999 |
| EP | 1 066 711 | 12/1999 | WO | WO 00/07695 | 2/2000 |
| | | | WO | WO 00/17178 | 3/2000 |

Signed and Sealed this

Seventeenth Day of August, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,646,141 B2
DATED : November 11, 2003
INVENTOR(S) : Hofen, Willi et al.

It is certified that error appears in the above-identified patent and that said Letters Patent is hereby corrected as shown below:

<u>Title page</u>
Item [73], Assignees, should read as follows: -- Degussa AG, Düsseldorf (DE); Uhde GmbH, Dortmund (DE) --

Signed and Sealed this

Eighth Day of February, 2005

JON W. DUDAS
*Director of the United States Patent and Trademark Office*